(12) United States Patent
Wagh et al.

(10) Patent No.: US 9,241,905 B2
(45) Date of Patent: Jan. 26, 2016

(54) PHARMACEUTICAL COMPOSITIONS OF CEFIXIME

(75) Inventors: Sanjay Chhagan Wagh, Pune (IN); Bharat Raghunath Metkar, Pune (IN); Makarand Krishnakumar Avachat, Pune (IN); Himadri Sen, Pune (IN)

(73) Assignee: LUPIN LIMITED, Mumbai (IN)

( * ) Notice: Subject to any disclaimer, the term of this patent is extended or adjusted under 35 U.S.C. 154(b) by 1278 days.

(21) Appl. No.: 12/297,026

(22) PCT Filed: Mar. 23, 2007

(86) PCT No.: PCT/IN2007/000121
§ 371 (c)(1),
(2), (4) Date: Mar. 4, 2009

(87) PCT Pub. No.: WO2007/119249
PCT Pub. Date: Oct. 25, 2007

(65) Prior Publication Data
US 2010/0009955 A1   Jan. 14, 2010

(30) Foreign Application Priority Data
Apr. 13, 2006  (IN) .............................. 330/KOL/2006

(51) Int. Cl.
*A61K 31/546* (2006.01)
*A61K 9/10* (2006.01)
*A61K 9/00* (2006.01)
*A61K 31/43* (2006.01)
*A61K 31/545* (2006.01)

(52) U.S. Cl.
CPC ................ *A61K 9/10* (2013.01); *A61K 31/546* (2013.01); *A61K 9/0095* (2013.01); *A61K 31/43* (2013.01); *A61K 31/545* (2013.01); *Y10S 514/97* (2013.01)

(58) Field of Classification Search
CPC ..... A61K 9/10; A61K 31/546; A61K 9/0095; A61K 31/43; A61K 31/545; Y10S 514/97
See application file for complete search history.

(56) References Cited

U.S. PATENT DOCUMENTS

| 4,079,138 | A | 3/1978 | Lin et al. |
| 4,409,214 | A | 10/1983 | Takaya et al. |
| 5,776,926 | A | 7/1998 | Bolz et al. |
| 2005/0131079 | A1* | 6/2005 | Pujara ........................... 514/777 |

FOREIGN PATENT DOCUMENTS

EP    0 685 232    12/1995

OTHER PUBLICATIONS

Asiri et al , International Journal of Clinical Pharmacology and Therapeutics, 2005, vol. 43 (10), pp. 499-504, abstract only.*
Niwa et al. , Biol. Phar. Bull., 2004, vol. 27 (1), pp. 97-99.*

* cited by examiner

*Primary Examiner* — Savitha Rao
(74) *Attorney, Agent, or Firm* — Merchant & Gould P.C.

(57) ABSTRACT

A pharmaceutical suspension formulation comprising a dose greater than 100 mg/5 ml Cefixime and pharmaceutically acceptable excipients.

15 Claims, No Drawings

PHARMACEUTICAL COMPOSITIONS OF CEFIXIME

This application is a National Stage Application of PCT/IN2007/000121, filed Mar. 23, 2007, which claims benefit of Serial No. 330/KOL/2006, filed Apr. 13, 2006 in India and which application(s) are incorporated herein by reference. To the extent appropriate, a claim of priority is made to each of the above disclosed applications.

FIELD OF THE INVENTION

The present invention relates to pharmaceutical suspension formulation comprising a new strength of Cefixime 200 mg/5 ml.

BACKGROUND OF THE INVENTION

Cefixime is a semi synthetic cephalosporin antibiotic for oral administration. It was first disclosed in U.S. Pat. No. 4,409,214 by Fujisawa Corporation, Japan.

It has a bactericidal action and the mechanism of action is based on inhibition of bacterial cell wall synthesis.

It is indicated for the treatment of infections caused by various gram—positive and gram—negative organisms chiefly uncomplicated urinary tract infections caused by E. coli and P. mirabilis, otitis media caused by H. influenza, M. catarrhalis and S. pyogenes, acute bronchitis and exacerbations of chronic bronchitis caused by S. pneumonia and H. influenza. It is also indicated for uncomplicated gonorrhea caused by N. gonorrhea. It is one of the most prescribed drugs for pediatric use.

Cefixime as a drug is poorly soluble in water. From the point of view of bioavailability, the preferred form of administration of sparingly soluble medicaments such as beta lactam antibiotics is often an aqueous suspension. Cefixime, given orally, is about 40%-50% absorbed whether administered with or without food.

Children 12 years of age or younger receive, e.g., about 8 mg of Cefixime/kg of body weight each day. The recommended dose can be administered alternatively all at once or divided into 2 single doses (e.g., about 4 mg of Cefixime/kg of body weight in the morning and evening). An increase in the daily dose to 2.×6 mg of Cefixime/kg of body weight is possible depending on the severity and the location of the infection. Adults and children above 12 years of age may receive 400 mg of Cefixime each day. The recommended daily dose may be administered alternatively all at once or divided into 2 single doses (in the morning and evening). The dose should be reduced for patients with distinctly impaired renal function.

Solid dosage forms such as tablets and capsules have certain disadvantages since they have to disintegrate in the gastrointestinal tract and then the medicament has to dissolve before it can be absorbed, thus leading to slower absorption as compared to that of the suspension dosage form and also the absorption is less than the suspension dosage form leading to bioequivalence issues. Also, certain patient populations such as pediatrics and geriatrics have difficulty in swallowing tablets and capsules, and there is a practical limit to the size, and therefore the dose, that can be swallowed.

The oral suspension dosage forms have certain advantages over the above mentioned dosage forms especially in population segments such as pediatrics and geriatrics who have problems in swallowing the solid dosage forms. Further The oral suspension dosage form produces average peak concentrations approximately 25%-50% higher than the conventional tablets. The area under the time versus concentration curve is greater by approximately 10%-25% with the oral suspension than with the conventional tablet after doses of 100 to 400 mg, when tested in normal adult volunteers.

U.S. Pat. No. 4,079,138 by American Home Products Corporation describe a permanent suspension with a non-aqueous basis as vehicle for active substances, which are sensitive to hydrolysis.

U.S. Pat. No. 5,776,926 by Merck discloses Cefixime compositions in the form of non-aqueous suspensions.

Cefixime is currently available in a number of different formulations in various strengths for adult and pediatric patients, for example as tablets comprising 200 mg and 400 mg Cefixime and as oral suspension comprising 100 mg/5 ml Cefixime.

In some patient population the compliance for the currently available oral suspension is low due to requirement of dosing greater than 100 mg in certain disease conditions. Lack of availability of a oral suspension dosage form comprising greater than 100 mg/5 ml cefixime leads to low compliance rates. This is due to multiple dosing required leading to low compliance rates (e.g.; spillage).

There is a need to develop a higher strength oral suspension in unit dose for improving the patient compliance and for reducing the frequency of dosing.

OBJECTS OF THE INVENTION

The object of the invention is to provide a suspension dosage form comprising an unit dose greater than 100 mg/5 ml and not more than 400 mg/5 ml of Cefixime and pharmaceutically acceptable excipients.

The principal object of the invention is to provide a suspension dosage form consisting essentially an unit dose of 200 mg/5 ml of Cefixime and pharmaceutically acceptable excipients.

Another object of the invention is to provide a suspension dosage form comprising Cefixime, wherein the said new suspension strength 200 mg/5 ml is bioequivalent to suspension 2×100 mg/5 ml comprising Cefixime trihydrate marketed under the name of "Suprax®".

Another object of the present invention is to provide a method of treating acute bacterial otitis media, pharyngitis, tonsillitis, Acute and chronic bronchitis with a oral suspension of cefixime wherein said suspension form consists essentially of an unit dose of 200 mg/5 ml of Cefixime and pharmaceutically acceptable excipients.

Yet another object of the invention is to provide a method of uncomplicated urinary tract infections and gonorrhea with a oral suspension of cefixime wherein said suspension form consists essentially of an unit dose of 200 mg/5 ml of Cefixime and pharmaceutically acceptable excipients.

DETAILED DESCRIPTION OF THE INVENTION

The present invention provides for an oral suspension comprising a unit dose of greater than 100 mg/5 ml and not more than 400 mg/5 ml of cefixime.

In preferred embodiment the present invention provides for an oral, pharmaceutical suspension composition comprising Cefixime 200 mg/5 ml. In another embodiment the present invention provides for an oral, pharmaceutical suspension composition comprising Cefixime 200 mg/5 ml which is bioequivalent to a suspension dosage form of Cefixime 2×100 mg/5 ml marketed under the trade name of SUPRAX®.

The term Cefixime as used herein also denotes the various salt forms of Cefixime including the commonly used trihydrate salt form.

The term "oral suspension" includes within its scope but is not limited to compositions selected from the group consisting of pellets for suspension which can be coated or uncoated, granules for suspension, in the form of a unit dose packet (sometimes referred to in the art as a "sachet"), in the form of a suspension made from a unit dose packet, in the form of a powder for oral suspension, in the form of a dose sipping device and in the form of an oral suspension per se (liquid suspension) and combinations of these e.g. coated pellets filled in a dose sipping device or in a sachet. It is noted that when a unit dose packet is constituted, it is probably mainly in the form of a suspension if reconstituted according to directions, although the extent of suspension versus solution depends on a number of factors such as pH.

Preferred oral, pharmaceutical suspension compositions comprising Cefixime are in the form of powder for suspension.

The oral, pharmaceutical suspension composition can additionally comprise of at least one excipient depending upon the dosage form e.g. whether as pellets or as granules for suspension and so on. The excipient can be one or more selected from the group consisting of diluents, sweeteners, viscosity enhancing agents, dispersing agents, preservatives, flavoring agents and the like. One excipient can perform more than one function.

Diluents include, but are not limited to, sucrose, sorbitol, xylitol, dextrose, fructose, malitol, sugar potassium, aspartame, saccharin, saccharin sodium, and mixtures thereof. A preferred diluent of the present invention is sucrose. Diluents can also be used as sweetener.

Suitable sweeteners include, but are not limited to, natural sweeteners such as sugars e.g. fructose, glucose, sucrose, sugar alcohols such as mannitol, sorbitol or mixtures thereof and artificial sweeteners such as sodium saccharine, sodium cyclamate and aspartame.

The term "viscosity enhancer," as used herein, refers to an agent or a mixture of agents that increases the thickness of a liquid thereby keeping the active ingredient suspended to allow accurate dosing. Viscosity enhancers include, but are not limited to, xantham gum, guar gum, acacia, alginic acid, sodium alginate, propylene glycol alginate, povidone, carbomer, salts of carboxymethylcellulose, methylcellulose, ethylcellulose, hydroxyethyl cellulose, hydroxypropyl cellulose, hydroxypropyl methylcellulose, bentonite, polydextrose, carrageenan, sucrose, sorbitol, xylitol, dextrose, fructose, malitol, gelatin, tragacanth, a polyvinyl alcohol, cetearyl alcohol, colloidal silicon dioxide and mixtures thereof. A preferred viscosity enhancer of the present invention is xantham gum.

Dispersing agents include, but are not limited to, colloidal silicon dioxide and surfactants, wherein the surfactant is used alone or as an admixture with one or more surfactant. Combinations of colloidal silicon dioxide with one or more surfactants can also be used.

The term "flavoring agent," as used herein, refers to an agent or a mixture of agents that adds flavor to a mixture. Flavoring agents include, but are not limited to, artificial strawberry flavor, art banana flavor and artificial cream flavor. A preferred flavoring agent of the present invention is strawberry flavor.

The term "preservative," as used herein, refers to an agent or mixture of agents that is used to protect a composition against antimicrobial (e.g., yeast, mold, bacteria) activity. Preservatives include, but are not limited to, sodium benzoate, benzoic acid, ethylenediaminetetraacetic acid, sorbic acid, benzethonium chloride, benzalkonium chloride, bronopol, butyl paraben, methyl paraben, ethylparaben, propyl paraben, thiomerosol, sodium propionate, chlorhexidine, chlorobutanol, chlorocresol, cresol, imidurea, phenol, phenylmercuric salts, potassium sorbate, propylene glycol, and mixtures thereof. A preferred preservative of the present invention is sodium benzoate.

All these excipients can be used at levels well known to the persons skilled in the art. The oral suspension compositions can be prepared by means well known to those skilled in the art.

The application of the invention can be seen by the following, non limiting examples:

Example 1

| Cefixime Suspension 200 mg/5 ml | |
|---|---|
| Ingredients | Quantity (mg) |
| Cefixime equivalent to Cefixime anhydrous | 200.00 |
| Xanthan gum | 10.00 |
| Sodium Benzoate | 10.00 |
| Colloidal silicon dioxide | 25.00 |
| Strawberry flavor | 25.00 |
| Sucrose | 2230.00 |
| Total weight | 2500.00 |

Brief Manufacturing Process:

Sift Cefixime and sucrose separately through suitable screen. Also sift other excipients like xanthan gum, colloidal silicon dioxide, sodium benzoate and strawberry flavor. Cefixime and the above excipients are milled with approximately 20% quantity of total sucrose.

All the excipients along with the drug are loaded in a blender and blended for specified period of time.

Bioequivalence Study

A bioequivalence study was carried out using the suspension (Test) comprising Cefixime 200 mg/5 ml as prepared in Example 1 against the commercially available oral suspension "SUPRAX®" (Cefixime, Reference) using twenty-five healthy human volunteers.

A 10 ml of the reference product was administered with 5 ml of the test product.

The bioequivalence data for this study is shown below in Table 1. The study was monitored in terms of the AUC and $C_{max}$ achieved with the test product and reference product. AUCs are plots of serum concentrations of Cefixime along the ordinate (Y-axis) against time on the abscissa (X-axis). Generally, the values for AUC represent a number of values taken from all the subjects in a population and are, therefore, mean values averaged over the entire population. Cmax, the observed maximum in a plot of serum level concentration of Cefixime (Y-axis) versus time (X-axis) is likewise an average value. The ratios of the log transformed mean values for $C_{max}$ and AUC for the test and reference product (T/R ratio) is a measure of the bioequivalence between the test and reference product. Values between 80 and 125% for the 90% Confidence Intervals of these ratios indicate bioequivalence as recommended by the USFDA.

TABLE 1

Comparative Bioequivalence fasting study data of Cefixime suspension 200 mg/5 ml against commercially available suspension formulation "SUPRAX ®" (Cefixime) 2 × 100 mg/5 ml n = 25.

| Pharmacokinetic Parameters | Log Trans-formed T/R Ratio of Least Square Means | 90% CI of log Transformed Data |
|---|---|---|
| Cmax | 103.5 | 95.32-112.34 |
| $AUC_{0-t}$ | 106.2 | 96.79-116.56 |
| $AUC_{0-inf}$ | 105.7 | 96.72-115.62 |

From the results of this study we can conclude that Cefixime suspension 200 mg/5 ml suspension exhibits bioequivalence to that of the marketed suspension formulation "SUPRAX®" (Cefixime) 2×100 mg/5 ml.

Thus, this invention provides a pharmaceutical suspension composition comprising Cefixime 200 mg/5 ml, which when administered in humans demonstrates an AUC and $C_{max}$ for Cefixime which is substantially equivalent to the AUC and $C_{max}$ obtained with twice the dose of an oral suspension formulation comprising Cefixime trihydrate marketed under the name of "Suprax®" is administered to humans.

As used herein, the term "substantially equivalent" means that the two products are bioequivalent within the framework of the guidelines for bioequivalence recommended by the USFDA as already elaborated earlier.

Thus, this invention also provides for a method of achieving bioequivalence between a new suspension dosage form of Cefixime 200 mg/5 ml and a suspension comprising Cefixime 100 mg/5 ml.

The embodiments of the invention in which an exclusive property or privilege is claimed are defined as follows:

1. A suspension dosage form of Cefixime comprising:
   a unit dose of 200 mg/5 ml of Cefixime;
   0.4 wt-% xanthan gum; and
   1 wt-% colloidal silicon dioxide;
   wherein said suspension dosage form is bioequivalent to the commercially available Cefixime suspension formulation of 2×100 mg/5 ml.

2. The suspension dosage form of claim 1, further comprising a pharmaceutically acceptable excipient; the pharmaceutically acceptable excipient selected from sweetener, flavoring agent, preservative, or mixture thereof.

3. The suspension dosage form of claim 2, wherein the sweetener is mannitol, sorbitol sodium saccharine, sodium cyclamate, or aspartame.

4. The suspension dosage form of claim 2, wherein the flavoring agent is strawberry flavor, banana flavor, or artificial cream flavor.

5. The suspension dosage form of claim 2, wherein the preservative is sodium benzoate, benzoic acid, ethylenediaminetetraacetic acid, sorbic acid, benzethonium chloride, benzalkonium chloride, bronopol, butyl paraben, methyl paraben, ethylparaben, propyl paraben, thiomerosol, sodium propionate, chlorhexidine, chlorobutanol, chlorocresol, cresol, imidurea, phenol, phenylmercuric salts, potassium sorbate, propylene glycol, or mixtures thereof.

6. A method of treating a subject having acute bacterial otitis media, pharyngitis, tonsillitis, acute bronchitis, or chronic bronchitis, the method comprising:
   administering to the subject the oral suspension dosage form of claim 1.

7. A method of treating a subject having an uncomplicated urinary tract infection, gonorrhea, or both, the method comprising:
   administering to the subject the oral suspension dosage form of claim 1.

8. The suspension dosage form of claim 1, further comprising 0.4 wt-% sodium benzoate.

9. A suspension dosage form of Cefixime consisting of:
   a unit dose of 200 mg/5 ml of Cefixime;
   0.4 wt-% xanthan gum;
   1 wt-% colloidal silicon dioxide; and
   sweetener, flavoring agent, preservative, or mixture thereof;
   wherein said suspension dosage form is bioequivalent to the commercially available Cefixime suspension formulation of 2×100 mg/5 ml.

10. The suspension dosage form of claim 9, wherein the sweetener is mannitol, sorbitol sodium saccharine, sodium cyclamate, or aspartame.

11. The suspension dosage form of claim 9, wherein the flavoring agent is strawberry flavor, banana flavor, or artificial cream flavor.

12. The suspension dosage form of claim 9, wherein the preservative is sodium benzoate, benzoic acid, ethylenediaminetetraacetic acid, sorbic acid, benzethonium chloride, benzalkonium chloride, bronopol, butyl paraben, methyl paraben, ethylparaben, propyl paraben, thiomerosol, sodium propionate, chlorhexidine, chlorobutanol, chlorocresol, cresol, imidurea, phenol, phenylmercuric salts, potassium sorbate, propylene glycol, or mixtures thereof.

13. The suspension dosage form of claim 9, wherein the preservative is 0.4 wt-% sodium benzoate.

14. A method of treating a subject having acute bacterial otitis media, pharyngitis, tonsillitis, acute bronchitis, or chronic bronchitis, the method comprising:
   administering to the subject the suspension dosage form of claim 9.

15. A method of treating a subject having an uncomplicated urinary tract infection, gonorrhea, or both, the method comprising:
   administering to the subject the suspension dosage form of claim 9.

* * * * *